United States Patent [19]
Navot et al.

[11] Patent Number: 6,063,042
[45] Date of Patent: May 16, 2000

[54] METHOD FOR DIAGNOSIS OF MENORRHAGIA MENSTRUAL CYCLE DISORDERS AND THEIR CAUSES

[76] Inventors: Nir Navot, 1 Hapaamon Street, Rosh Haayin; Ronnie Botton, 8 Tabenkin Street, Herzlia, both of Israel

[21] Appl. No.: 09/182,193

[22] Filed: Oct. 30, 1998

Related U.S. Application Data

[63] Continuation-in-part of application No. PCT/US98/20257, Sep. 28, 1998.

[51] Int. Cl.$^7$ ........................................... A61B 5/00
[52] U.S. Cl. ........................................... 600/584; 604/361
[58] Field of Search .................... 600/549, 573, 600/584; 604/11, 317, 318, 358, 361

[56] References Cited

U.S. PATENT DOCUMENTS

| | | | |
|---|---|---|---|
| 3,460,123 | 8/1969 | Bass | 604/361 |
| 3,841,333 | 10/1974 | Zalucki | |
| 4,583,546 | 4/1986 | Garde | 604/361 |
| 5,542,914 | 8/1996 | Van Iten | 604/11 |
| 5,882,931 | 3/1999 | Petersen | 600/584 |
| 5,904,671 | 5/1999 | Navot et al. | 604/361 |

*Primary Examiner*—Max Hindenburg
*Attorney, Agent, or Firm*—Mark M. Friedman

[57] ABSTRACT

A system for diagnosis of menorrhagia, menstrual cycle disorders and their causes comprising (a) a device including (i) a menses-collecting article, e.g., insertable into a vagina; (ii) at least one sensor for sensing a presence of menses in one or more distinct locations of the menses-collecting article; and (iii) a reporter being in data communication with the at least one sensor for reporting the presence of menses in the one or more distinct locations of the menses-collecting article, the reporter serving for recording information relating to the presence of menses in the one or more distinct locations of the menses-collecting article in a time related manner; and (b) an analyzing unit for receiving the information from the reporter and for analyzing the information.

10 Claims, 1 Drawing Sheet

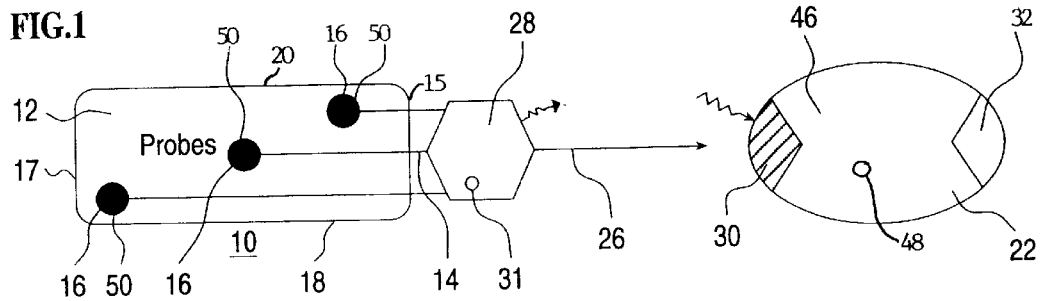
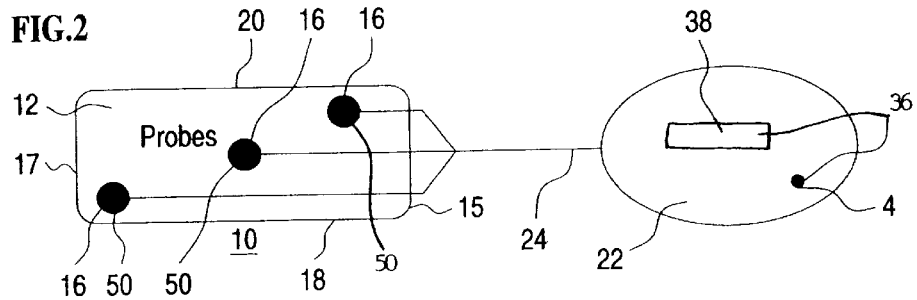
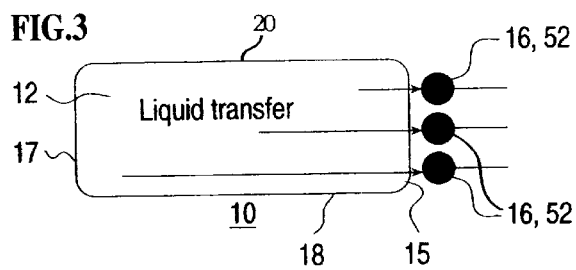
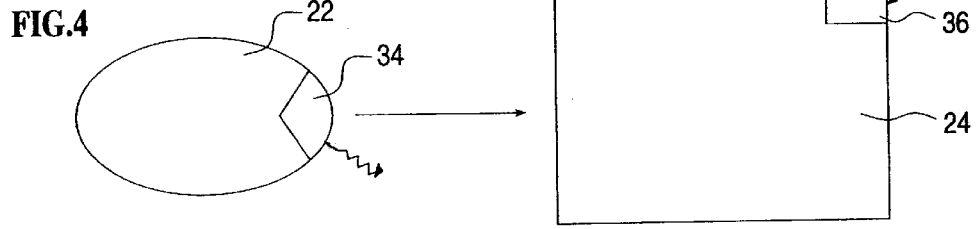

METHOD FOR DIAGNOSIS OF MENORRHAGIA MENSTRUAL CYCLE DISORDERS AND THEIR CAUSES

This is a continuation-in-part of international application PCT/US98/20257, Sep. 28, 1998.

FIELD AND BACKGROUND OF THE INVENTION

The present invention relates, in general, to the diagnosis of menorrhagia, menstrual cycle disorders and their causes, and more particularly to a device, method and system for diagnosis of menorrhagia, menstrual cycle disorders and their causes.

In most women menses occurs every 21 to 35 days, has a duration of 4 to 6 days and a volume of 30 to 80 ml. Excessive uterine bleeding (menorrhagia) is a common and distressing symptom. Its effect on the patient herself and her surroundings is great. Menorrhagia affects 15% to 20% of otherwise healthy women and can be indicative of cancer, endocrinological disorders or gynecological diseases.

Menorrhagia is technically defined as menses lasting longer than 7 days or a blood loss volume in excess of 60 to 80 ml. With volumes greater than 80 ml, the risk of sever anemia becomes rather high. In theory, menorrhagia can be precisely defined by the duration and volume of uterine bleeding; in fact, a woman's report of excessive bleeding, whether she describes it as "large amounts", "clotting, "flooding", or "heavy use of tampons", has little correlation with the actual amount of blood lost. Fewer than half of women who complained of excessive bleeding actually had menstrual blood loss of more than 80 ml per menstrual period [Treatment decisions in the management of Menorrhagia, Jo Ann Rosenfeld, Medscape Women's Health 2(1), 1997].

There is thus a widely recognized need for, and it would be highly advantageous to have an objective tool with which a clinician could measure the length of a period and the volume of blood loss associated with menses. Such a tool will assist in the diagnosis of gynecological disorders that eventuate in changes in the length of the period and the volume of blood loss associated therewith, see Chapple A, Ling M and May C. (1998) General practitioners' perceptions of the illness behavior and health needs of South Asian women with menorrhagia. *Ethn. Health.* 3(1–2):81–93, which is incorporated by reference as if fully set forth herein

SUMMARY OF THE INVENTION

Thus, it is one object of the present invention is to provide a device, method and system for diagnosing menorrhagia, menstrual cycle disorders and their causes.

It is another object of the present invention to provide a device, method and system by which a clinician could measure the length of a period and the volume of blood loss associated therewith, thus facilitating the diagnosis of gynecological disorders that eventuate in changes in the length of a period and the volume of blood loss associated therewith.

It is yet another object of the present invention to provide such device, method and system which would not further burden the woman who undergoes a diagnostic procedure therewith and would enable the ongoing logging of information relating to the length of a period and the volume of blood loss associated therewith that would be later retrieved and analyzed by the clinician.

It is still yet another object of the present invention to provide a device, method and system by which a clinician could detect at least one component present in normal and/or abnormal vaginal secretion, including, but not limited to, compounds, microorganisms and/or toxins.

According to one aspect of the present invention there is thus provided a device for diagnosis of menorrhagia, menstrual cycle disorders and their causes, comprising (a) a menses-collecting article, e.g., insertable into a vagina or used externally for menses collection, such as a sanitary napkins; (b) at least one sensor for sensing a presence of menses in one or more distinct locations of the menses-collecting article for indicating a volume of menses secreted; and (c) a reporter being in data communication with the at least one sensor for reporting the presence of menses in the one or more distinct locations of the menses-collecting article.

According to further features in preferred embodiments of the invention described below, the reporter serves for recording information relating to the presence of menses in the one or more distinct locations of the menses-collecting article as an indication of the volume of menses collected in a time related manner. To this end the reporter includes a timer to time the replacements of the menses collecting article and the time took for the article to collect a determined volume of menses.

According to still further features in the described preferred embodiments the reporter serves for communicating the information to an analyzing unit.

According to another aspect of the present invention there is provided a system for diagnosis of menorrhagia, menstrual cycle disorders and their causes, comprising (a) a device including (i) a menses-collecting article, such as a tampon, or a sanitary napkin; (ii) at least one sensor for sensing a presence of menses in one or more distinct locations of the menses-collecting article indicating the volume of menses secreted; and (iii) a reporter being in data communication with the at least one sensor for reporting the presence of menses in the one or more distinct locations of the menses-collecting article, the reporter serving for recording information relating to the presence of menses in the one or more distinct locations of the menses-collecting article as an indication of the volume of menses secreted in a time related manner; and (b) an analyzing unit for receiving the information from the reporter and for analyzing the information.

According to yet another aspect of the present invention there is provided method of diagnosing menorrhagia, menstrual cycle disorders and their causes, comprising the steps of (a) inserting into a vagina or placing in direct contact therewith a device including (i) a menses-collecting article; (ii) at least one sensor for sensing a presence of menses in one or more distinct locations of the menses-collecting article as an indication of the quantity of menses secreted; and (iii) a reporter being in data communication with the at least one sensor for reporting the presence of menses in the one or more distinct locations of the menses-collecting article; and (b) retrieving and analyzing information relating to the presence of menses in the one or more distinct locations of the menses-collecting article.

According to further features in preferred embodiments of the invention described below, the data communication between the at least one sensor and the reporter is effected by direct communication.

According to still further features in the described preferred embodiments the data communication between the at least one sensor and the reporter is effected by remote communication According to still further features in the described preferred embodiments the remote communication is effected by a transmitter being in communication with the at least one sensor and a compatible receiver being in communication with the reporter.

According to still further features in the described preferred embodiments the reporter further serves for alerting a user when a pre condition is met. According to still further features in the described preferred embodiments the reporter includes an interface connectable to the analyzing unit for communicating the information.

According to still further features in the described preferred embodiments the reporter includes a transmitter and the analyzing unit includes a receiver for communicating the information from the reporter to the analyzing unit.

According to still further features in the described preferred embodiments the at least sensor includes a sensing unit being in the menses-collecting article.

According to still further features in the described preferred embodiments the at least one sensor includes a sensing unit being out of the menses-collecting article, whereas at least one liquid transfer article engaged within the menses-collecting article serves for directing the menses or a fraction thereof from the menses-collecting article to the at least one sensor.

According to still further features in the described preferred embodiments at least one of the sensors is designed to sense a presence of a specific component of the menses.

The present invention successfully addresses the shortcomings of the presently known configurations by providing an objective tool with which a clinician can monitor the length of a period and the volume of blood loss associated therewith, thus facilitating the diagnosis of gynecological disorders that eventuate in changes in the length of a period and the volume of blood loss associated therewith.

BRIEF DESCRIPTION OF THE DRAWINGS

The invention herein described, by way of example only, with reference to the accompanying drawings, wherein:

FIGS. 1–3 are simplified schematic depictions of a device for diagnosing menorrhagia and menstrual cycle disorders according to the present invention;

FIG. 4 is a simplified schematic depiction of the communication between a reporter and an analyzing unit in a system for diagnosing menorrhagia and menstrual cycle disorders according to the present invention; and FIG. 5 is a simplified schematic depiction of a conductive wetness sensor employed with the device for diagnosing menorrhagia and menstrual cycle disorders according to the present invention.

DESCRIPTION OF THE PREFERRED EMBODIMENTS

The present invention is of a device, system and method which can be used to objectively measure the length of a period and the volume of blood loss associated therewith, as well as the presence and level of components associated therewith in healthy and disease conditions. Specifically, the present invention can be used to diagnose menorrhagia and menstrual cycle disorders and their causes.

The principles and operation of a device, system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1–5 illustrate several preferred embodiments according to the present invention.

According to one aspect of the present invention there is thus provided a device for diagnosis of menorrhagia and menstrual cycle disorders, which is referred to hereinbelow as device 10.

Device 10 includes a menses-collecting article 12 either insertable into a vagina, like a tampon, or designed to be placed externally in contact therewith, like a sanitary napkin. Article 12, is preferably made of a rolled and compressed absorbent material, such as cotton, covered by a nonwoven material. Alternatively, article 12 is non-absorbing, as described, for example, in U.S. Pat. Nos. 4,799,929; 5,743, 893; and 5,295,984, which are incorporated by reference as if fully set forth herein. Article 12 is typically substantially cylindrical, and is preferably equipped with a removing floss 14 protruding from its distal end 15 in a fashion similar to a conventional tampon device.

Device 10 according to the present invention further includes at least one sensor 16 (three sensors 16 are shown in FIGS. 1–3) for sensing the presence of menses, and/or a component or components thereof as further detailed hereinunder, in one or more distinct locations (three respective locations are shown in FIGS. 1–3) of menses-collecting article 12.

It is known that menses is deposited in the vagina from the cervix of the uterus and flows downward in the vagina toward the introitus. Thus the proximal end 17 of article 12 becomes wet first, and, in addition, the bottom side 18 of article 12 wets before the top 20 thereof, due to the tendency of menses to flow along the floor of the vagina. Thus, by carefully selecting the locations within article 12 which are sensed by each of sensors 16, e.g., proximal-bottom, medial and distal-top locations, one can follow the wetness progressing within article 12 as described above. In fact, by knowing the capacity of article 12, one can use such a sensors arrangement to determine at any time point the amount of menses secreted and absorbed since the insertion of device 10 into the vagina.

Device 10 according to the present invention further includes a reporter 22. Reporter 22 is in data communication with sensor(s) 16 and serves for reporting the presence of menses and/or a component thereof, in the one or more distinct locations of menses-collecting article 12. According to a preferred embodiment of the present invention reporter 22 further serves for recording information relating to the presence of menses in the one or more distinct locations of menses-collecting article 12 in a time related manner. As used herein the term "time" refers also to the term "date". As further detailed hereinunder, according to a preferred embodiment of the present invention, reporter 22 further serves for communicating the information to an analyzing unit 24 (FIG. 4).

An analyzing unit, such as unit 24, in combination with device 10 form a system for diagnosis of menorrhagia and menstrual cycle disorders according to the present invention. Thus, the system includes a device for diagnosis of menorrhagia and menstrual cycle disorders, such as device 10 described herein which includes (i) a menses-collecting article, e.g., insertable into a vagina; (ii) at least one sensor for sensing a presence of menses in one or more distinct locations of the menses-collecting article, to thereby measure the volume of menses secreted; and (iii) a reporter being in data communication with the at least one sensor for reporting the presence of menses in the one or more distinct locations of the menses-collecting article, the reporter serves for recording information relating to the presence of menses in the one or more distinct locations of the menses-collecting article in a time related manner to thereby monitor the volume of menses secreted; and an analyzing unit 24 for receiving the information from the reporter and for analyzing the information.

Unit 24 can be, for example, a personal computer including a dedicated software for such analysis. The dedicated software can be developed by one ordinarily skilled in the art and is therefore only briefly described herein. In general, the dedicated software should be able to extract and analyze the information received from the sensors and provide the clinician with processed data relating, for example, to the duration of menses secretion, rate of secretion, total volume of secretion, presence and level of specific menses components, etc. The processed data can be presented textually or graphically, on a screen and can also preferably be printed. It is also preferably stored for future retrieval.

According to yet another aspect of the present invention there is provided method of diagnosis of menorrhagia, menstrual cycle disorders and their causes. The method is effected by executing the following method steps, in which, in a first step a device for diagnosing menorrhagia and menstrual cycle disorders, such as device 10 described herein, is inserted into or placed externally in contact with a vagina, the device includes (i) a menses-collecting article; (ii) at least one sensor for sensing a presence of menses in one or more distinct locations of the menses; and (iii) a reporter being in data communication with the at least one sensor for reporting the presence of menses in the one or more distinct locations of the menses-collecting article; and, in a second step information relating to the presence of menses in the one or more distinct locations of the menses-collecting article is retrieved and analyzed.

The following sections describe several preferred embodiments of device 10 according to the present invention.

Thus, according to a preferred embodiment, and as specifically shown in FIG. 2, the data communication between sensor(s) 16 and reporter 22 is effected, as indicated by 24, by direct communication, such as wire communication.

However, according to another preferred embodiment, and as specifically shown in FIG. 1, the data communication between sensor(s) 16 and reporter 22 is effected, as indicated by 26, by remote communication. The remote communication is effected by a transmitter 28 being in communication with sensor(s) 16 and a compatible receiver 30 being in communication with reporter 22. Transmitter 28 can be designed to be removeably attached at distal end 15 of article 12 or to the underwear of the user, or to her body, for multiple uses. A suitable interface is formed in this case to provide for connection between transmitter 28 and sensor(s) 16. Transmitter 28 can include a power source 31, such as a battery, for its operation, which power source 31 can be used to power sensor(s) 16 as well. The remote communication can be effected by the well known radio frequency technology or alternatively the surface acoustic waves (SAW) technology, as for example described in U.S. Pat. Nos. 5,760,525 and 4,625,208, which are incorporated by reference as if fully set forth herein.

Transmitter 28 can be remotely energized by a remote energizing device 32, formed with, for example, reporter 22. Energizing can be effected every predetermined time interval and be of sufficient energy to activate sensor(s) 16 and transmitter 28 to sense and transmit the sensed information in such time intervals, say every several seconds, minutes or hours. Energizing can be effected by radio frequency (RF).

According to another preferred embodiment of the present invention reporter 22 further serves for alerting the user when a pre designated condition, such as that the capacity of article 12 to further absorb menses is low and it should be replaced, is met. Reporting according to the present invention can be effected in a variety of ways. For example, reporter 22 can include a signaling device 36, such as, but not limited to, a display 38 for reporting the information in a textual, graphical or numerical manner, and/or an alarming device 40, including, for example, a light source, e.g., a light emitting diode (LED), a sound generating device, or a vibrating or pricking device, for alarming the user. In a preferred embodiment reporting can be effected by more than a single reporting mode and a mode selector is provided to enable the user to select a desired reporting mode, for example, awakening modes (vibration, pricking or sound) during night time and intimate or personal modes (display, light or vibration) during day time. In any case, reporter 22 includes a power source 48, to provide power for its operation. It preferably further includes an on/off control button.

It will be appreciated that for diagnostic purposes a plurality of articles 12 are used during a single period. Each such article 12 is preferably communicating with a single reporter 22, which accumulates the data from all of which for further analysis. Each such replacement is recorded by reporter 22.

According to still another preferred embodiment of the present invention, reporter 22 is a portable device carried or worn by the user. In a preferred embodiment it includes a wrist band 46 (proximal parts thereof are shown in FIG. 1) and may therefore be worn on a wrist of the user. Alternatively, it can be attached to the underwear of the user to her thigh or abdomen via, for example, an adhesive surface thereof.

According to yet another preferred embodiment of the present invention reporter 22 includes an interface connectable to analyzing unit 24 for communicating the information thereto. Alternatively, reporter 22 includes a transmitter 34 and analyzing unit 24 includes a receiver 36 for communicating the information from reporter 22 to analyzing unit 24.

According to still another preferred embodiment of the present invention, at least one of sensor(s) 16 is a conductive wetness sensor which includes, as shown in FIG. 5, two metal plates 40 and an absorbent substance 42 intimately disposed therebetween, such that when absorbent substance 42 becomes wet, sensor 20 becomes conductive. Alternatively, a wetness sensor can be designed to have two metal wires whose ends are held together by a microscopic flax string, whereas when the string becomes wet it elongates, allowing the ends to separate thus braking a circuit.

As specifically shown in FIGS. 1–2, according to an embodiment of the present invention, each sensor(s) 16 includes a sensing unit 50 being in absorbent menses-collecting article 12. Alternatively, as specifically shown in FIG. 3, each of sensor(s) 16 includes a sensing unit 52, located external to menses-collecting article 12, whereas at least one liquid transfer article, engaged within menses-collecting article 12 serves for directing the menses from various locations in menses-collecting article 12 to sensor(s) 16.

According to still further features in the described preferred embodiments at least one of sensor(s) 16 is designed to sense the presence of a specific component included in the secreted menses. One example is given hereinabove, wherein the component is humidity or water. Other examples include sensors adapted of detecting one or more substances such as, but not limited to blood, sugars, minerals, ions, salts, proteins, toxins, microorganisms, and the like, or one or more parameters, such as, but not limited to, temperature, wetness or pH. Miniaturized temperature, pH and other ions or salt sensors are well known in the art. For example, a temperature sensor is adapted at sensing a heat magnitude and converting it into an electrical parameter (e.g., resistance, voltage, etc.) of a magnitude corresponding to the heat. Thermistors thus operating are distributed, for example, by Beta Therm Cat. #1K7A1. A glucose sensor according to the present invention is preferably a glucose oxidase based glucose sensor which includes a potentiostat and an electronic chip for quantifying the glucose level in the menses. The operation of these components is well known in the art. Prior art glucose sensors are distributed by, for example, LifeScan Inc. and MediSense Inc. USA. Other sensors are also known in the art and can be miniaturized to fit into or be attached to article 12.

The present invention thus provides the first objective tool with which a clinician can measure the length of a period and the volume of blood loss associated therewith. The clinician can also be informed regarding the composition of the menses.

Although the invention has been described in conjunction with specific embodiments thereof, it is evident that many alternatives, modification and variations be apparent to those skilled in the art. Accordingly, it is intended to embrace all such alternatives, modifications and variations that fall within the spirit and broad scope of the appended claims.

What is claimed is:

1. A method of diagnosing menorrhagia and menstrual cycle disorders comprising the steps of:
    (a) inserting into a vagina or externally contacting therewith a device including:
        (i) a menses-collecting article;
        (ii) at least one sensor for sensing a presence of menses in one or more distinct locations of said menses-collecting article; and
        (iii) a reporter being in data communication with said at least one sensor for reporting said presence of menses in said one or more distinct locations of said menses-collecting article; and
    (b) retrieving and analyzing information relating to said presence of menses in said one or more distinct locations of said menses-collecting article.

2. The method of claim 1, wherein said data communication between said at least one sensor and said reporter is effected by direct communication.

3. The method of claim 1, wherein said data communication between said at least one sensor and said reporter is effected by remote communication.

4. The method of claim 3, wherein said remote communication is effected by a transmitter being in communication with said at least one sensor and a compatible receiver being in communication with said reporter.

5. The method of claim 1, wherein said reporter further serves for alerting a user when a pre designated condition is met.

6. The method of claim 1, wherein step (b) is effected by an analyzing unit, whereas said reporter includes an interface connectable to said analyzing unit for communicating said information.

7. The method of claim 1, wherein said reporter includes a transmitter, whereas step (b) is effected by an analyzing unit which includes a receiver for communicating said information from said reporter to said analyzing unit.

8. The method of claim 1, wherein said at least one sensor includes a sensing unit being in said menses-collecting article.

9. The method of claim 1, wherein said at least one sensor includes a sensing unit being out of said menses-collecting article, whereas at least one liquid transfer article engaged within said menses-collecting article serves for directing said menses from said menses-collecting article to said at least one sensor.

10. The method of claim 1, wherein at least one of said sensors is designed to sense a presence of a specific component of said menses.

* * * * *